United States Patent [19]
Sakaguchi et al.

[11] Patent Number: 5,780,692
[45] Date of Patent: Jul. 14, 1998

[54] PROCESS FOR PRODUCING OPTICALLY ACTIVE BENZHYDROL COMPOUNDS

[75] Inventors: Minzo Sakaguchi; Takashi Imai; Takashi Miura; Tetsuro Yamazaki, all of Kanagawa, Japan

[73] Assignee: Takasago International Corporation, Tokyo, Japan

[21] Appl. No.: 772,525

[22] Filed: Dec. 24, 1996

[30] Foreign Application Priority Data

Dec. 28, 1995 [JP] Japan .................. 7-343199

[51] Int. Cl.[6] .......... C07C 33/46; C07C 33/34; C07C 35/21; C07C 35/22
[52] U.S. Cl. .......... 568/814; 568/816; 568/817; 568/807; 568/809; 568/812
[58] Field of Search .................. 568/816, 817, 568/326, 331, 332, 807, 809, 812, 814

[56] References Cited

U.S. PATENT DOCUMENTS 3,968,147  7/1976  Solodar .

FOREIGN PATENT DOCUMENTS 0718265  6/1996  European Pat. Off. .

OTHER PUBLICATIONS

M.P. Balfe, M.A. Doughty, J. Kenyon, and R. Poplet, Alkyl–Oxygen Fission in Carboxylic Esters. Part II. Derivatives of p–Methoxybenzhydrol. *J. Chem. Soc.*, 1942, 605–611.

D. Seebach, A. K. Beck, S. Roggo, and A. Wonnacott, Enantioselektive Addition von Arylgruppen an aromatische Aldehyde mit Aryltitan–Binaphtol–Derivaten. *Chem. Ber.*, 118, 3673–3682 (1985).

Ji–Tao Wang, X. Fan, X. Feng, and Yi–Min Qian, Studies on Enantioselective Addition of Chiral Titanium Reagents to Aromatic Aldehydes, *Synthesis*, 1989, 291–292.

Ohkuma et al., J. Am. Soc. 1995, 117, 2675–6.

Journal of the American Chemical Society, vol. 117, No. 9, Mar. 8, 1995, pp. 2675–2676 T. Ohkuma et al, "Practical enantioselective hydrogenation of aromatic ketones".

*Primary Examiner*—Gary Geist
*Assistant Examiner*—Karl J. Puttlitz, Jr.
*Attorney, Agent, or Firm*—Sughrue, Mion, Zinn, Macpeak & Seas, PLLC

[57] ABSTRACT

A process for producing a benzhydrol compound (II) which comprises hydrogenating a benzophenone compound (I) in the presence of a hydrogenation catalyst consisting of a transition metal complex, a base and an optically active diamine compound:

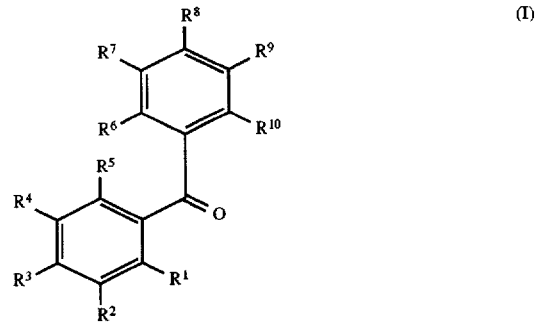

(I)

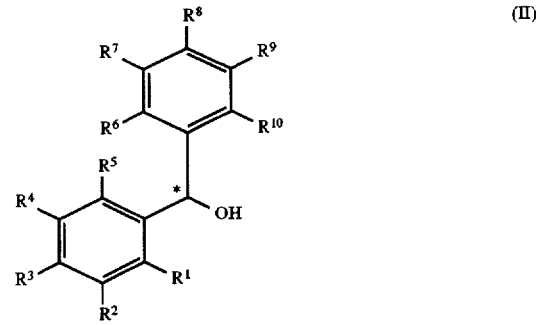

(II)

wherein $R^1$ to $R^{10}$ each represents H, OH, $C_{1-4}$ alkyl, $C_{1-4}$ alkoxy, $C_{1-4}$ alkanoyl, etc., $R^2$ and $R^3$, and $R^8$ and $R^9$ may form —CH=CH—CH=CH—, or any two of $R^1$ to $R^9$ adjacent to each other may be bonded to thereby form —OCH$_2$O— or —(CH$_2$)$_3$—. By using this process, optically active benzhydrol compounds which have a high purity and are useful as, for example, intermediates in the synthesis of drugs can be produced by simple procedures.

6 Claims, No Drawings

PROCESS FOR PRODUCING OPTICALLY ACTIVE BENZHYDROL COMPOUNDS

FIELD OF THE INVENTION

This invention relates to a process for producing optically active benzhydrol compounds. More particularly, it relates to a novel and practically useful process for producing optically active benzhydrol compounds which are useful in various purposes, for example, as intermediates in the synthesis of drugs or liquid crystal materials.

BACKGROUND OF THE INVENTION

Known processes for synthesizing optically active alcohols include: 1) methods wherein enzymes (bread yeast, etc.) are employed; and 2) those wherein carbonyl compounds are asymmetrically hydrogenated with the use of metal complexes. Regarding the latter asymmetric hydrogenation methods, in particular, there have been presented a number of proposals, for example, (1) a method of the asymmetric hydrogenation of a carbonyl compound having a functional group with the use of an optically active ruthenium catalyst described in detail in *Asymmetric Catalysis In Organic Synthesis*, 56–82, (1994), Ed. R. Noyori; (2) a hydrogen transfer reduction with the use of ruthenium, rhodium and iridium asymmetric complex catalysts described in *Chem, Rev.*, vol. 92, 1051–1069 (1992); (3) a method of the asymmetric hydrogenation of tartaric acid by using a modified nickel catalyst described in *Yu-Kagaku (Oil Chemistry)*, 828–831 (1980) and *Advances in Catalysis*, vol. 32, 215 (1983), Ed. by Y.Izumi; (4) a method of asymmetric hydrosilylation described in *Asymmetric Synthesis*, vol. 5, chap. 4 (1985), Ed. J. D. Morrison and *J. Organomet. Chem.*, vol. 346, 413–424 (1988); (5) a method of borane reduction in the presence of an asymmetric ligand described in *J. Chem. Soc., Perin Trans. I.*, 2039–2044 (1985) and *J. Am. Chem. Soc.*, vol. 109, 5551–5553 (1987); and (6) a method of asymmetric hydrogenation of acetophenone by using potassium hydroxide, an optically active diamine and a ruthenium asymmetric complex described in *J. Am. Chem. Soc.*, vol. 117, 2675–2676 (1995).

Among the above-mentioned methods for synthesizing optically active alcohols, however, those with the use of enzymes have some disadvantages, i.e., troublesome operations should be employed therein, the reaction substrates are limited and the obtained alcohols are restricted in the absolute configuration. On the other hand, the methods with the use of asymmetric hydrogenation catalysts of transition metals are in sufficient in the reaction rate. In these methods, furthermore, attentions should be paid to the substrate specificity. That is to say, they are unexpectedly less efficacious in the case of relatively simple carbonyl compounds.

There have been reported a number of transition metal complexes to be used in the asymmetric hydrogenation of carbonyl compounds. Although these catalysts are considerably efficacious in the asymmetric hydrogenation of carbonyl compounds (i.e., the reaction substrates) which are ketones having an aromatic ring group and an aliphatic group (acetophenone derivatives, etc.), it is known that the hydrogenation per se can hardly proceed in the case where the substrates are ketones having two aromatic ring groups.

On the other hand, it is expected that benzhydrol compounds, which are useful in various purposes, for example, as intermediates in the synthesis of drugs or liquid crystal materials, might be produced by hydrogenating benzophenone compounds by using a transition metal complex. However, this process falls within the above-mentioned category and, therefore, any good result can be scarcely achieved.

When a compound of a specific absolute configuration is exclusively useful as in the case of a drug, in particular, the obtained product cannot be utilized unless it is an optically active compound, even though the hydrogenation has been successfully completed. Accordingly, the above-mentioned methods are seemingly not applicable to the synthesis of such specific ketones.

Accordingly, an object of the present invention is to provide a novel process wherein a benzophenone compound is asymmetrically hydrogenated by a simple procedure to thereby give an optically active benzhydrol compound of the desired absolute configuration at a high optical purity.

Under these circumstances, the present inventors have conducted extensive studies. As a result, they have successfully found out that the above-mentioned object can be achieved by hydrogenating a benzophenone compound in the presence of an asymmetric hydrogenation catalyst consisting of a transition metal complex, a base and an optically active amine compound, thus completing the present invention.

SUMMARY OF THE INVENTION

Accordingly, the present invention provides a process for producing an optically active benzhydrol compound represented by formula (II):

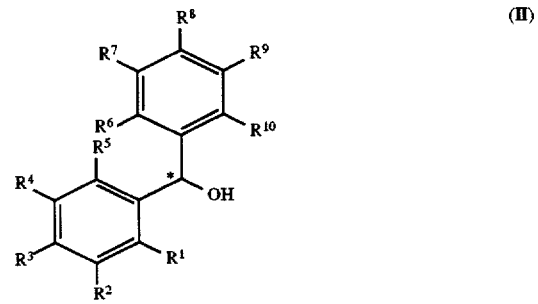

(II)

wherein $R^1$, $R^5$, $R^6$ and $R^{10}$ are the same or different and each represents a hydrogen atom, a halogen atom, a hydroxyl group, a lower alkyl group having 1 to 4 carbon atoms, a lower alkoxy group having 1 to 4 carbon atoms or a lower alkanoyl group having 1 to 5 carbon atoms; $R^2$, $R^3$, $R^4$, $R^7$, $R^8$ and $R^9$ are the same or different and each represents a hydrogen atom, a halogen atom, a hydroxyl group, a lower alkyl group having 1 to 4 carbon atoms, a lower alkoxy group having 1 to 4 carbon atoms, a lower alkanoyl group having 1 to 5 carbon atoms or an amino group optionally substituted by a lower alkyl group, a lower alkanoyl group or a lower alkoxycarbonyl group, $R^2$ and $R^3$, and $R^8$ and $R^9$ may be bonded to each other to thereby form —CH=CH—CH=CH—, and any two of $R^1$ to $R^9$ adjacent to each other may be bonded to thereby form —OCH$_2$O— or —(CH$_2$)$_3$—; and * shows the location of an asymmetric carbon atom;

which comprises hydrogenating a benzophenone compound represented by formula (I):

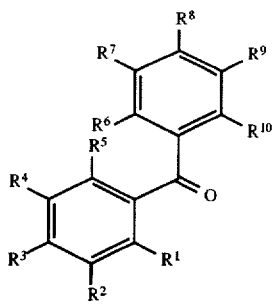

(I)

wherein $R^1$, $R^2$, $R^3$, $R^4$, $R^5$, $R^6$, $R^7$, $R^8$, $R^9$ and $R^{10}$ are each as defined above;

in the presence of a hydrogenation catalyst consisting of a transition metal complex, a base and an optically active diamine compound.

DETAILED DESCRIPTION OF THE INVENTION

In the above-mentioned benzophenone compound serving as the substrate in the reaction, examples of the halogen atom as $R^1$, $R^5$, $R^6$ and $R^{10}$ include fluorine, chlorine, bromine and iodine atoms. Among all, chlorine and bromine atoms are particularly preferable and a chlorine atom is still preferable therefor.

Examples of the lower alkyl group having 1 to 4 carbon atoms include methyl, ethyl, propyl, isopropyl, n-butyl, isobutyl and tert-butyl groups and a methyl group is preferable therefor.

Examples of the lower alkoxy group having 1 to 4 carbon atoms include methoxy, ethoxy, propyloxy, isopropyloxy, n-butyloxy, isobutyloxy and tert-butyloxy groups and a methoxy group is preferable therefor.

Examples of the lower alkanoyl group having 1 to 5 carbon atoms include formyl, acetyl, ethylcarbonyl, propylcarbonyl, isopropylcarbonyl, butylcarbonyl, isobutylcarbonyl and pivaloyl groups and acetyl and pivaloyl groups are preferable therefor.

Examples of the halogen atom, lower alkyl group having 1 to 4 carbon atoms, lower alkoxy group having 1 to 4 carbon atoms and lower alkanoyl group having 1 to 5 carbon atoms, and the lower alkyl group and lower alkanoyl group which are the substituent of the amino group in $R^2$, $R^3$, $R^4$, $R^7$, $R^8$ and $R^9$ are the same as those cited above. Also, preferable examples thereof are the same as those cited above.

Examples of the lower alkoxycarbonyl group which is the substituent of the amino group include those having 1 to 4 carbon atoms such as methoxycarbonyl, etoxycarbonyl, propoxycarbonyl, isopropyloxycarbonyl, butoxycarbonyl, isobutoxycarbonyl and tert-butyloxycarbonyl groups. In particular, a tert-butyloxycarbonyl group is preferable therefor.

Examples of the substituted amino group include a mono-substituted amino group having one substituent and a disubstituted amino group having two substituents and the former is preferred therefor to the latter.

Examples of the benzophenone compound (I) serving as the starting compound in the present invention are those listed in the following Table 1, though the present invention is not restricted thereto. In Table 1, Me stands for a methyl group.

TABLE 1

| Compound | Substituent on the ring carrying $R^6$ etc. | Substituent on the ring carrying $R^1$ etc. |
|---|---|---|
| 1 | $R^6$ = OMe | $R^1$ = Cl |
| 2 | $R^6$ = $R^7$ = OMe | " |
| 3 | $R^6$ = $R^8$ = OMe | " |
| 4 | $R^6$ = $R^9$ = OMe | " |
| 5 | $R^6$ = $R^{10}$ = OMe | " |
| 6 | $R^6$ = $R^8$ = $R^{10}$ = OMe | " |
| 7 | $R^6$, $R^7$ = —OCH$_2$O— | " |
| 8 | $R^7$, $R^8$ = —OCH$_2$O— | " |
| 9 | $R^6$ = OMe | $R^1$ = $R^3$ = Cl |
| 10 | $R^6$ = F | $R^1$ = Cl |
| 11 | $R^6$ = Br | " |
| 12 | $R^8$ = Cl | " |
| 13 | $R^7$ = Cl | " |
| 14 | $R^6$ = Cl | " |
| 15 | $R^6$ = $R^8$ = Cl | " |
| 16 | $R^6$ = Cl | $R^1$ = F |
| 17 | " | $R^1$ = Br |
| 18 | $R^6$ = CF$_3$ | $R^1$ = Cl |
| 19 | — | " |
| 20 | $R^8$ = Cl | — |
| 21 | $R^6$ = Cl | — |
| 22 | " | $R^1$ = Me |
| 23 | " | $R^3$, $R^4$ = —(CH$_2$)$_3$— |
| 24 | $R^6$ = F | — |
| 25 | $R^6$ = Cl | $R^1$ = OMe |
| 26 | — | $R^1$ = CF$_3$ |
| 27 | $R^8$ = NH$_2$ | — |
| 28 | $R^8$ = NHMe | — |
| 29 | $R^6$ = Me | — |
| 30 | $R^7$ = Me | — |
| 31 | $R^8$ = Me | — |
| 32 | $R^6$ = OMe | — |
| 33 | $R^8$ = OMe | — |
| 34 | $R^6$ = OH | — |
| 35 | $R^7$ = OH | — |
| 36 | $R^8$ = OH | — |
| 37 | $R^8$, $R^9$ = —CH=CH—CH=CH— | — |
| 38 | $R^6$ = COOMe | — |
| 39 | — | — |

As the benzophenone compound (I), it is preferable to use one carrying a substituent which is a halogen atom or a lower alkyl group having 1 to 4 carbon atoms, still preferably a chlorine atom or a methyl group, at the 2-position of the phenyl ring.

The benzophenone compound (I) can be synthesized in accordance with the method described in D. A. Walsh, *Synthesis*, p. 677 (1980) or a method similar thereto.

Particular examples of the transition metal complex to be used in the present invention include complexes of transition metals belonging to the group VIII in the periodic table, namely, complexes of ruthenium, rhodium, iridium, palladium, platinum, etc. Among all, ruthenium complexes are particularly suitable therefor. Examples of the ruthenium complexes include those represented by the following formulae (III) to (VI):

[Ru$_2$X$_4$(L)$_2$](A)    (III)

wherein X represents a halogen atom; L represents an optically active phosphine ligand; and A represents a tertiary amine;

[RuX(E)(L)]X    (IV)

wherein X and L are each as defined above; and E represents an optionally substituted benzene or p-cymene;

|Ru(G)₂(L)| (V)

wherein L is as defined above; and G represents a halogen atom or an acetoxy group; and

|RuX(L))⁺J⁻ (VI)

wherein X and L are each as defined above; and J⁻ represents $BF_4^-$, $ClO_4^-$, $PF_6^-$ or $BPh_4^-$ wherein Ph represents a phenyl group.

Examples of the halogen atoms in the above complexes include fluorine, chlorine, bromine and iodine atoms. Among all, chlorine, bromine and iodine atoms are preferable and a chlorine atom is still preferable therefor.

Examples of the tertiary amine include tri(lower alkyl) amines, in particular, trimethylamine, triethylamine, tripropylamine, etc. Among all, triethylamine is preferable therefor.

Examples of the substituent of the optionally substituted benzene include lower alkyl groups having 1 to 4 carbon atoms, lower alkoxy groups having 1 to 4 carbon atoms, alkoxycarbonyl groups and halogen atoms. Among all, lower alkyl groups having 1 to 4 carbon atoms are preferable therefor.

Examples of the substituted benzene include toluene, xylene, trimethylbenzene (in particular, mesitylene), durene, hexamethylbenzene, ethylbenzene, tert-butylbenzene, cymene (in particular, p-cymene), cumene, methyl benzoate, methyl methylbenzoate, methyl chlorobenzoate, anisole, methylanisole, chlorobenzene, dichlorobenzene, trichlorobenzene, bromobenzene, fluorobenzene, etc.

Examples of the complexes (III) to (VI) are as follows.

Complex (III): |Ru₂Cl₄(L)₂|NEt₃, |Ru₂Br₄(L)₂|NEt₃, |Ru₂I₄(L)₂|NEt₃.

Complex (IV): |RuI(p-cymene)(L)|I, |RuCl(p-cymene)(L)|Cl, |RuBr(p-cymene)(L)|Br, (RuI(benzene)(L)|I, |RuCl(benzene)(L)|Cl, |RuBr(benzene)(L)|Br, |RuI(toluene)(L)|I, |RuCl(xylene)(L)|Cl, |RuBr(mesitylene)(L)|Br, |RuI(hexamethylbenzene)(L)|I.

Complex (V): |RuBR₂(L)|, |Ru(OAc)₂(L)| (Ac represents an acetyl group).

Complex (VI): |RuCl(L)|⁺BF₄⁻, |RuCl(L)|⁺ClO₄⁻, |RuCl(L)|⁺PF₆⁻, |RuCl(L)|⁺BPh₄⁻.

Among the above-mentioned complexes (III) to (VI), the complexes (III) and (IV) are preferable and the complexes (III) are still preferable.

In the above complexes, L represents an optically active phosphine ligand. Particular examples thereof are compounds represented by the following general formula (VII) or (VIII).

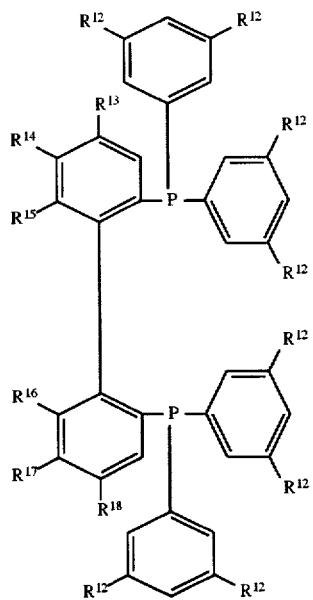
(VII)

wherein $R^{12}$ represents a lower alkyl group having 1 to 4 carbon atoms; and $R^{13}$, $R^{14}$, $R^{15}$, $R^{16}$ $R^{17}$ and $R^{18}$ are the same or different and each represents a hydrogen atom, a lower alkyl group having 1 to 4 carbon atoms, a lower alkoxy group having 1 to 4 carbon atoms or a halogen atom, or $R^{14}$ and $R^{15}$, and $R^{16}$ and $R^{17}$ may be bonded together to thereby form each a ring.

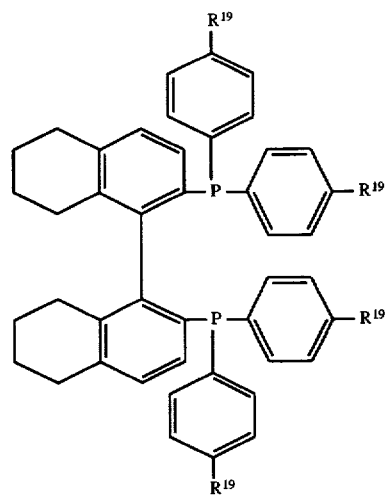
(VIII)

wherein $R^{19}$ represents a hydrogen atom or a lower alkyl group having 1 to 4 carbon atoms.

Examples of the lower ($C_{1-4}$) alkyl groups represented by $R^{12}$ to $R^{19}$ in the above-mentioned ligands (VII) and (VIII) include methyl, ethyl, propyl, isopropyl, n-butyl, isobutyl and tert-butyl groups. Among all, a methyl group is preferable therefor.

Examples of the lower ($C_{1-4}$) alkoxy substituents include methoxy, ethoxy, propyloxy, isopropyloxy, n-butyloxy, isobutyloxy and tert-butyloxy groups. Among all, a methoxy group is preferable therefor.

Examples of the halogen substituents include fluorine, chlorine, bromine and iodine atoms. Among all, chlorine and bromine atoms are preferable therefor.

In the ligand (VII), $R^{14}$ and $R^{15}$, and $R^{16}$ and $R^{17}$ may be bonded together to thereby form each a ring, for example, a 6-membered ring composed of —CH=CH—CH=CH—, —(CH₂)₄, etc.

As particular examples of the ligand (VII), optically active phosphine ligands represented by the following general formulae (IX) and (X) may be cited.

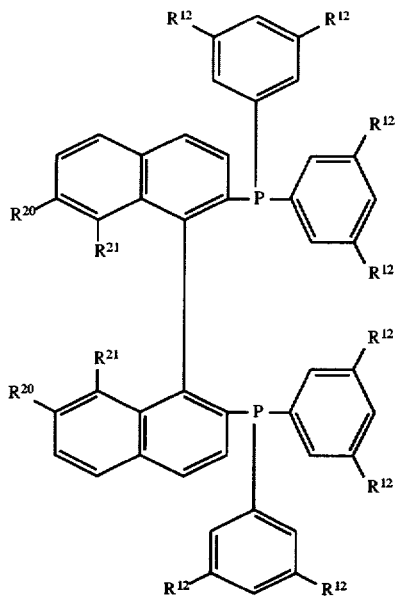

(IX)

wherein $R^{12}$ is as defined above; and $R^{20}$ and $R^{21}$ represent each a hydrogen atom or a methyl group, or $R^{20}$ and $R^{21}$ may be bonded together to thereby form —CH=CH—CH=CH—; and

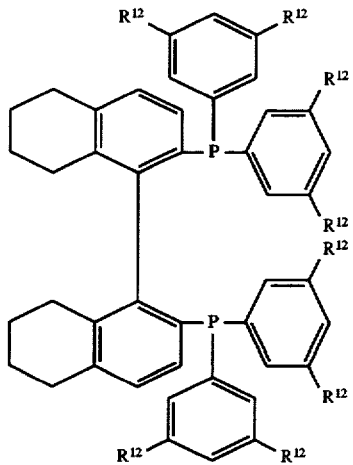

(X)

wherein $R^{12}$ is as defined above.

In the substituted phenyl group bonded to the phosphorus atom of such an optically active phosphine ligand, it is preferable that the substituents are located at the m-positions, as in the cases of the substituents $R^{12}$ in the ligands (VII), (IX) and (X). By selecting the appropriate positions, it is possible to obtain a target compound at a high optical purity (% e.e.).

The optically active phosphine ligands include those having binaphthyl skeletons such as the ligand (IX) and those having octahydrobinaphthyl skeletons such as the ligand (VIII). It is preferable to use one having a binaphthyl skeleton and thus a target compound can be obtained at a high conversion ratio and a high optical purity (% e.e.).

Accordingly, it is the most desirable to use an optically active phosphine ligand which has substituents located at the m-positions and a binaphthyl skeleton.

The above-mentioned ligands (VII) to (X) can be synthesized by publicly known methods. For example, an optically active biphenyl ligand (VII) wherein neither $R^{14}/R^{15}$ nor $R^{16}/R^{17}$ forms any ring can be obtained by performing the reaction in accordance with the following reaction scheme and then optically resolving the reaction product, as described in JP-A-59-65051 (the term "JP-A" as used herein means an "unexamined published Japanese patent application"):

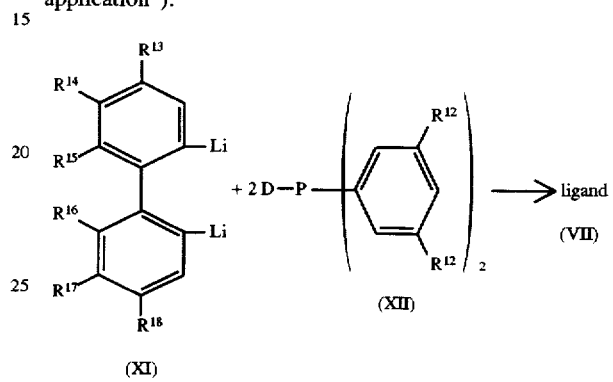

(XI) (XII)

wherein $R^{12}$, $R^{13}$, $R^{14}$, $R^{15}$, $R^{16}$, $R^{17}$ and $R^{18}$ are each as defined above; and D represents a leaving group.

That is to say, a 2,2'-lithium-1,1'-biphenyl compound (XI) is reacted with a di(3,5-disubstituted phenyl)phosphine compound (XII) and the product thus obtained is optically resolved to thereby give a ligand (VII).

The ligands (VIII) and (X) can be synthesized in accordance with, for example, the following reaction scheme as described in JP-A-4-139140:

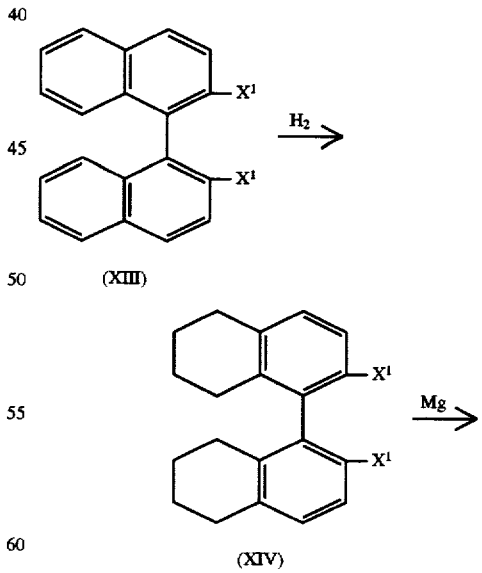

(XIII)

(XIV)

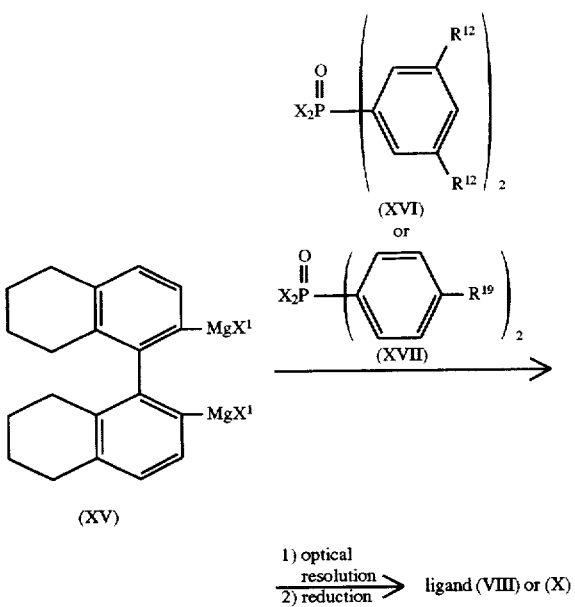

(XV)

1) optical resolution
2) reduction
⟶ ligand (VIII) or (X)

wherein $R^{12}$ and $R^{19}$ are as defined above; and $X^1$ and $X_2$ represent each a halogen atom.

That is to say, a 2,2'-halogeno-1,1'-binaphthyl (XIII) is hydrogenated in the presence of a ruthenium/carbon catalyst to thereby give a 2,2'-halogeno-5,5',6,6',7,7',8,8'-octahydro-1,1'-binaphthyl (XIV). Then this compound (XIV) is converted into a Grignard reagent (XV) by reacting with metal magnesium. The Grignard reagent (XV) is condensed with a diphenylphosphino halide compound (XVI) or (XVII) and then the product thus obtained is optically resolved. After reduction of the optically pure product thus obtained, a ligand (VIII) or (X) can be obtained.

As described above, the ligands (VII) or (VIII) are preferable as the optically active phosphine ligand. More particularly, the ligands (IX), from among the ligands (VII), are still preferable followed by the ligands (VIII) and the ligands (X) from among the ligands (VII).

The ligands (VII) are roughly classified into biphenyl ligands wherein neither $R^{14}/R^{15}$ nor $R^{16}/R^{17}$ forms any ring and those wherein $R^{14}/R^{15}$ and/or $R^{16}/R^{17}$ form ring(s). The latter ones are preferred to the former ones.

Examples of the ligands with the ring formation include the ligands (IX) and (X). The ligands (IX) are particularly preferable therefor.

In the ligands (VII), particular examples of the biphenyl ligands (VII) wherein neither $R^{14}/R^{15}$ nor $R^{16}/R^{17}$ forms any ring include 6,6'-dimethyl-2,2'-bis|di(3,5-dimethylphenyl)phosphino|-1,1'-biphenyl and 6,6'-dimethoxy- 2,2'-bis|di(3,5-dimethylphenyl)phosphino|-1,1'-biphenyl.

Particular examples of the ligands (IX), i.e., the ligands (VII) wherein $R^{14},R^{15}$ and/or $R^{16}/R^{17}$ form ring(s), include 2,2'-bis|di(3,5-di(lower alkyl)phenyl)phosphino|-1,1'-binaphthyls such as 2,2'-bis|di(3,5-dimethylphenyl)phosphino|-1,1'-binaphthyl (DM-BINAP); 7,7'-dimethyl-2,2'-bis|di(3,5-di(lower alkyl)phenyl)phosphino|-1,1'-binaphthyls such as 7,7'-dimethyl-2,2'-bis|di(3,5-dimethylphenyl)phosphino|-1,1'-binaphthyl; 8,8'-dimethyl-2,2'-bis|di(3,5-di(lower alkyl)phenyl)phosphino|-1,1'-binaphthyls such as 8,8'-dimethyl-2,2'-bis|di(3,5-dimethylphenyl)phosphino|-1,1'-binaphthyl; and 3,3'-bis|di(3,5-di(lower alkyl)phenyl)phosphino|-4,4'-biphenanthryl such as 3,3'-bis|di(3,5-dimethylphenyl)phosphino|-4,4'-biphenanthryl. Among all, 2,2'-bis|di(3,5-di(lower alkyl)phenyl)phosphino|-1,1'-binaphthyls are preferable and 2,2'-bis|di(3,5-dimethylphenyl)phosphino|-1,1'-binaphthyl (DM-BINAP) is particularly preferable therefor. The term "lower alkyl" as used herein means a lower alkyl having 1 to 4 carbon atoms.

Examples of the ligands (X), i.e., the ligands (VIII) or (VII) wherein $R^{14}/R^{15}$ and/or $R^{16}/R^{17}$ form ring(s) include 2,2'-bis(diphenylphosphino)-5,5',6,6',7,7',8,8'-octahydro-1,1'-binaphthyl (OcH-BINAP). 2,2'-bis|di(p-tolyl)phosphino|-5,5',6,6',7,7',8,8'-octahydro-1,1'-binaphthyl (OcH-Tol-BINAP) and 2,2'-bis|di(3,5-di(lower alkyl)phenyl)phosphino|- 5,5',6,6',7,7',8,8'-octahydro-1,1'-binaphthyls such as 2,2'-bis|di(3,5-dimethylphenyl)phosphino|-5,5',6,6',7,7',8,8'-octahydro-1,1'-binaphthyl (OcH-DM-BINAP). Among all, OcH-BINAP and 2,2'-bis|di(3,5-di(lower alkyl)phenyl)phosphino|-5,5',6,6',7,7',8,8'-octahydro-1,1'-binaphthyls are preferable therefor. The term "lower alkyl" as used herein means a lower alkyl having 1 to 4 carbon atoms.

These ligands occur each (R)- and (S)-isomers from which the desired one may be appropriately selected depending on the purpose.

In addition to the ones cited above, it is also possible to use the following optically active phosphine ligands.

2,2'-Bis(diphenylphosphino)-1,1'-binaphthyl (BINAP).

2,2'-Bis|di(p-tolyl)phosphino|-1,1'-binaphthyl (Tol-BINAP).

2,2'-Bis(dicyclohexylphosphino)-6,6'-dimethyl-1,1'-binaphthyl (BICHEP).

N,N'-Dimethyl-1-|1',2-bis(diphenylphosphino)-ferrocenyl| ethylamine (BPPFA).

2,3-Bis(diphenylphosphino)butane (CHIRAHOS).

1-Cyclohexyl-1,2-bis(diphenylphosphino)ethane (CYCPHOS).

1-Substituted-3,4-bis(diphenylphosphino)pyrrolidine (DEGPHOS).

(R,R)-2,3-o-Isopropylidene-2,3-dihydroxy-1,4-bis (diphenylphosphino)butane (DIOP).

(R,R)-1,2-Bis|(o-methoxyphenyl)phenylphosphino|ethane (DIPAMP).

Substituted-1,2-bis(phosphorano)benzene (DUPHOS).

(R,R)-5,6-Bis(diphenylphosphino)-2-norbornene (NORPHOS).

N,N'-Bis(diphenylphosphino)-N,N'-bis|(R)-1-phenylethyl|-ethylenediamine (PNNP).

(S)-1,2-Bis(diphenylphosphino)propane (PROPHOS).

(S,S)-2,4-Bis(diphenylphosphino)pentane (SKEWPHOS).

Particular examples of the transition metal complex to be used in the present invention include |Ru₂Cl₄(DM-BINAP)₂| NEt₃ (wherein Et represents an ethyl group), |Ru₂Cl₄(OcH-BINAP)₂|NEt₃, |Ru₂Cl₄(OcH-DM-BINAP)₂| NEt₃, [RuI(p-cymene) (DM-BINAP)|I, |RuCl(p-cymene)(DM-BINAP)|Cl, |RuBr(p-cymene) (DM-BINAP)|Br, |RuI(benzene)(DM-BINAP)|I, |RuCl(benzene) (DM-BINAP)|Cl, |RuBr(benzene)(DM-BINAP)|Br, |RuI (p-cymene)(OcH-BINAP)|I, |RuCl(p-cymene)(OcH-BINAP)|Cl, |RuBr(p-cymene)(OcH-BINAP)|Br, |RuI (benzene)(OcH-BINAP)|I, |RuCl(benzene)(OcH-BINAP)| Cl, |RuBr(benzene)(OcH-BINAP)|Br, [RuI(p-cymene) (OcH-DM-BINAP)|I, |RuCl(p-cymene)(OcH-DM-BINAP)| Cl, |RuBr(p-cymene)(OcH-DM-BINAP)|Br, |RuI (benzene)(OcH-DM-BINAP)|I, |RuCl(benzene)(OcH-DM-BINAP)|Cl, |RuBr(benzene)(OcH-DM-BINAP)|Br, |RuBr₂ (DM-BINAP)|, |RuBr₂(OcH-BINAP)|, |RuBr₂(OcH-DM-BINAP)|, |Ru(OAc)₂(DM-BINAP)|, |Ru(OAc)₂(OcH-BINAP)|, |Ru(OAc)₂(OcH-DM-BINAP)|, |RuCl(DM-BINAP)|⁺BF₄⁻, |RuCl(OcH-BINAP)|⁺BF₄⁻, |RuCl(OcH- DM-BINAP)|⁺BF₄⁻, |RuCl(DM-BINAP)|⁺ClO₄⁻, |RuCl(OcH-BINAP)|⁺ClO₄⁻, |RuCl(OcH-DM-BINAP)|⁺ClO₄⁻, |RuCl(DM-BINAP)|⁺PF₆⁻, |RuCl(OcH-BINAP)|⁺PF₆⁻ and |RuCl(OcH-DM-BINAP)|⁺PF₆⁻.

Among these transition metal complexes, preferable ones include |Ru₂Cl₄(DM-BINAP)₂|NEt₃, |Ru₂Cl4(OcH-BINAP)₂|NEt₃, |Ru₂Cl₄(OcH-DM-BINAP)₂|NEt₃, |RuI(p-cymene)(DM-BINAP)|I, |RuCl(p-cymene)(DM-BINAP)|Cl, |RuBr(p-cymene)(DM-BINAP)|Br, |RuI(benzene)(DM-BINAP)|I, |RuCl(benzene)(DM-BINAP)|Cl, |RuBr(benzene)(DM-BINAP)|Br, |RuI(p-cymene)(OcH-BINAP)|I, |RuCl(p-cymene)(OcH-BINAP)|Cl, |RuBr(p-cymene)(OcH-BINAP)|Br, |RuI(benzene)(OcH-BINAP)|I, |RuCl(benzene)(OcH-BINAP)|Cl, |RuBr(benzene)(OcH-BINAP)|Br, |RuI(p-cymene)(OcH-DM-BINAP)|I, |RuCl(p-cymene)(OcH-DM-BINAP)|Cl, |RuBr(p-cymene)(OcH-DM-BINAP)|Br, |RuI(benzene)(OcH-DM-BINAP)|I, |RuCl(benzene)(OcH-DM-BINAP)|Cl and |RuBr(benzene)(OcH-DM-BINAP)|Br, and still preferable ones include |RU₂Cl₄(DM-BINAP )₂|NEt₃, |Ru₂Cl₄ (OcH-BINAP)₂| NEt₃ and |Ru₂Cl₄(OcH-DM-BINAP)₂|NEt₃.

Although the amount of the transition metal complex to be used in the present invention varies depending on the reaction vessel, reaction type and economy, it may be employed at a molar ratio to the benzophenone compound (I), i.e., the reaction substrate of from 1/100 to 1/100,000, preferably from 1/500 to 1/10,000.

Examples of the base to be used in the asymmetric hydrogenation catalyst in the present invention include a compound represented by the following general formula (XVIII):

MY_n  (XVIII)

wherein M represents an alkali metal atom or an alkaline earth metal atom; Y represents a hydroxyl group, an alkoxyl group or a mercapto group; and n is 1 or 2; or a quaternary ammonium salt. It is particularly preferable to use the compound (XVIII) therefor, though the present invention is not restricted thereto.

Examples of the alkali metal atom in the base (XVIII) include lithium, sodium, potassium, rubidium and caesium. Sodium and potassium are preferable therefor and potassium is still preferable. Examples of the alkaline earth metal atom in the base (XVIII) include magnesium, calcium, strontium and barium and calcium is preferable therefor. An alkali metal atom is preferred to an alkaline earth metal.

Examples of the alkoxyl group include those having 1 to 4 carbon atoms such as methoxy, ethoxy, propoxy, isopropyloxy, n-butyloxy and tert-butyloxy groups and methoxy, isopropyloxy and tert-butyloxy groups are preferable therefor.

Particular examples of the base (XVIII) include potassium hydroxide, sodium hydroxide, cesium hydroxide, lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, potassium tert-butoxide and sodium thiomethoxide. Among all, sodium hydroxide, potassium hydroxide, potassium isopropoxide and potassium tert-butoxide are preferable therefor and potassium hydroxide and potassium tert-butoxide are still preferable.

The base may be used in an amount of from 0.001 to 0.5 mol equivalent, preferably from 0.01 to 0.5 mol equivalent and still preferably from 0.03 to 0.1 mol equivalent, to the benzophenone compound (I), i.e., the reaction substrate.

As the optically active diamine compound to be used in the asymmetric hydrogenation catalyst, it is preferable to employ a compound wherein two carbon atoms having amino and/or substituted amino groups are adjacent to each other (i.e., an ethylenediamine compound).

It is preferable to use therefor an optically active diamine compound wherein one or two of the carbon atoms having amino and/or substituted amino groups are asymmetric carbon atom(s) and one having two asymmetric carbon atoms is particularly preferable. For example, citation may be made of ethylenediamine compounds, propanediamine compounds, butanediamine compounds, cyclic hydrocarbon diamine compounds and phenylenediamine compounds. Among all, ethylenediamine compounds are preferable therefor.

More particularly, it is preferable to use an optically active diamine compound represented by, for example, the following general formula (XIX):

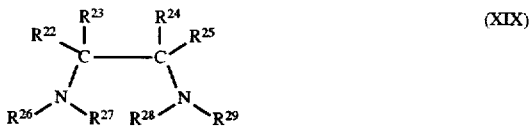

wherein $R^{22}$, $R^{23}$, $R^{24}$ and $R^{25}$ each represents a hydrogen atom, an alkyl group having 1 to 4 carbon atoms, a benzyl group, an aryl group or a cycloalkyl group having 5 to 7 carbon atoms, or $R^{23}$ and $R^{24}$ may be bonded together to thereby form a ring; and $R^{26}$, $R^{27}{}_1$, $R^{28}$ and $R^{29}$ each represents a hydrogen atom, an unsaturated hydrocarbon group, an aryl group or a sulfonyl group, provided that $R^{22}$ and $R^{23}$, and $R^{24}$ and $R^{25}$ are not the same as each other at the same time.

Examples of the alkyl group having 1 to 4 carbon atoms represented by the substituents $R^{22}$, $R^{23}$, $R^{24}$, $R^{25}$, $R^{26}$, $R^{27}$, $R^{28}$ and $R^{29}$ in the optically active diamine compound (XIX) include methyl, ethyl, propyl, isopropyl and tert-butyl groups. A methyl group is particularly preferable therefor.

Examples of the aryl group include optionally substituted phenyl and optionally substituted naphthyl groups. Among all, optionally substituted phenyl groups are preferable and a phenyl group is still preferable therefor. Examples of the substituted phenyl groups include those substituted by lower alkyl groups having 1 to 4 carbon atoms such as p-tolyl and 3,5-dimethylphenyl groups. A p-tolyl group is particularly preferable therefor.

Examples of the cycloalkyl group having 5 to 7 carbon atoms include cylopentyl, cyclohexyl and cycloheptyl groups. Among all, a cyclohexyl group is preferable therefor.

$R^{23}$ and $R^{24}$ may be bonded together to thereby form a ring. Examples of the ring include cyclohexyl and cycloheptane rings.

As the unsaturated hydrocarbon group, citation may be made of linear unsaturated hydrocarbon groups such as an allyl group.

Particular examples of such optically active diamine compounds include 1,2-diphenylethylenediamine, 1,2-cyclohexylethylenediamine, 2,3-butanediamine, 1,2-diaminocylohexane, 1,2-diaminocycloheptane, 1-methyl-2,2-diphenylethylenediamine, 1-isobutyl-2,2-diphenylethylenediamine, 1-isopropyl-2,2-diphenylethylenediamine, 1-methyl-2,2-di(p-methoxyphenyl)ethylenediamine, 1-isobutyl-2,2-di(p-methoxyphenyl)ethylenediamine, 1-isopropyl-2,2-di(p-methoxyphenyl)ethylenediamine, 1-benzyl-2,2-di(p-methoxyphenyl)ethylenediamine, 1-methyl-2,2- dinaphthylethylenediamine, 1-isobutyl-2,2-dinaphthylethylenediamine, 1-isopropyl-2,2-dinaphthylethylenediamine, etc. Among all, 1,2-diphenylethylenediamine is preferable therefor.

It is considered that the above-mentioned optically active diamine compound (XIX) wherein two of the carbon atoms having amino and/or substituted amino groups are asymmetric carbon atoms occurs in the form of four isomers, namely, (R,R)-, (S,S)-, (R,S)- and (S,R)-isomers. Among them, (R,R)- and (S,S)-isomers are preferable. Such an isomer may be appropriately selected depending on the purpose.

To select the isomer, it is important to consider the combination thereof with the optically active phosphine ligand in the transition metal complex to be employed. Although there are seemingly various combinations thereof, the most desirable combinations include the (R)-isomer of the optically active phosphine ligand with the (R,R)-isomer of the optically active amine compound, and the (S)-isomer of the optically active phosphine ligand with the (S,S)-isomer of the optically active amine compound. It is important to select such a combination to achieve a high asymmetric yield.

In the reaction of the present invention, the optically active amine compound may be used in an amount of from 1 to 20 mol equivalent, preferably from 4 to 12 mol equivalent to the transition metal complex.

In the present invention, it is essentially required to employ the three catalytic components (i.e., transition metal complex, base and optically active diamine compound) in order to perform the asymmetric hydrogenation reaction smoothly and achieve a high asymmetric yield. Unless all of these three components are employed, no optically active benzhydrol compound of a high purity can be obtained at a sufficiently high reaction activity.

The solvent to be used in the asymmetric hydrogenation of the benzphenone compound (I) may be an arbitrary one without restriction, so long as the reactants and the catalyst system can be solubilized thereby. Examples thereof include aromatic hydrocarbon solvents such as toluene and xylene; aliphatic hydrocarbon solvents such as heptane and hexane; halogenated hydrocarbon solvents such as methylene chloride; ether solvents such as diethyl ether and tetrahydrofuran; alcohol solvents such as methanol, ethanol, 2-propanol, butanol and benzyl alcohol; acetonitrile; and organic solvents having heteroatoms such as DMF (dimethylformamide) and DMSO (dimethyl sulfoxide). These solvents may be used either alone or as a mixture thereof. Since the reaction product is an alcohol, it is preferable to use an alcohol solvent and 2-propanol is particularly preferable therefor.

The amount of the solvent employed in the reaction is determined depending on the solubilities of the reaction substrate and economics. For example, when 2-propanol is used as the solvent, the reaction may be carried out at a low concentration (1% by volume or below) or in an almost solvent-free state in the cases of some substrates. However, it is preferable to use 2-propanol in an amount 2 to 5 times by volume as much as the reaction substrate.

The reaction of the present invention may be performed either batchwise or continuously. The reaction is carried out in the presence of hydrogen and the hydrogen pressure may be regulated to 1 to 100 atm, preferably from 20 to 50 atm. The reaction temperature preferably ranges from 20° to 90° C., still preferably from 35° to 60° C. The reaction time preferably ranges from 2 to 48 hours, still preferably from 16 to 30 hours.

To further illustrate the present invention in greater detail, and not by way of limitation, the following Examples will be given. In these Examples, spectra were measured by using the following instruments.

$^1$H-NMR spectrum: Model AM-400, manufactured by Bruker Inc. internal standard: tetramethylsilane, solvent: $CDCl_3$.

Mass spectrum (MS): M-80B mass spectrometer, manufactured by Hitachi, Ltd.

In each Example, the conversion ratio and optical purity of the product were measured by high performance liquid chromatography (HPLC) under the following conditions.

Conversion ratio:
High performance liquid chromatography: HITACHI L-4000.
  Column: INERTSIl DOS, 4.6×250 mm.
  Developer: acetonitrile/$H_2O$(90/10 by volume).
  Wavelength: 254 nm.
  Temperature: room temperature.
  Flow rate: 0.5 ml/min.

Optical purity:
High performance liquid chromatography: HITACHI 655A.
  Column: CIRAL CEL OD-H, 4.6×250 mm.
  Developer: hexane/2-propanol (80/20 by volume).
  Wavelength: 254 nm.
  Temperature: room temperature.
  Flow rate: 1 ml/min.

EXAMPLE 1

Asymmetric hydrogenation of 4-methylbenzophenone

Into a 100 ml stainless autoclave were fed a 0.2M solution of potassium hydroxide in 2-propanol (1.4 ml, containing 0.28 mmol of potassium hydroxide), (1S,2S)-1,2-diphenylethylenediamine (4.03 mg, 0.019 mmol), 4-methylbenzophenone (0.98 g, 5.0 mmol), 2-propanol (2.28 ml), benzene (1.23 ml) and $Ru_2Cl_4|(S)$-DM-BINAP| $_2NEt_3$ (9.07 mg, 0.00474 mmol) under a nitrogen atmosphere. Then hydrogen gas was supplied thereinto so as to achieve a hydrogen pressure of 50 atm. After stirring at a reaction temperature of 50° C. for 20 hours, the reaction mixture was returned to ordinary temperatures and then concentrated under reduced pressure.

1.01 g of the residue thus obtained was purified by silica gel column chromatography (developer: hexane/ethyl acetate=4/1 to 2/1 by volume) to thereby give optically active 4-methylbenzhydrol in the form of an oily product (0.871 g, yield: 88.0%). The optical purity of this product measured by high performance liquid chromatography was 98% e.e.

$^1$H-NMR (400 MHz, $CDCl_3$, δ ppm):
  2.21 (broad s, 1H), 2.33 (s, 3H), 5.81 (broad s, 1H), 7.1–7.4 (m, 9H).
ME (m/e): 198 ($M^+$).

EXAMPLES 2 TO 6

The reaction of Example 1 was repeated but using the starting compounds as listed in Table 2 and replacing the (1S,2S)-1,2-diphenylethylenediamine and $Ru_2Cl_4|(S)$-DM-BINAP$|_2NEt_3$ respectively by (1R,2R)-1,2-diphenylethylenediamine and $Ru_2Cl_4|(R)$-DM-BINAP$|_2NEt_3$ to thereby give the corresponding optically active hydrogenation products. Table 2 shows the results.

TABLE 2

| Example No. | Starting compound | Conversion ratio (%) | Optical purity (% e.e.) |
|---|---|---|---|
| 2 | 2-methylbenzophenone | 100 | >98.0 |
| 3 | 3-methylbenzophenone | 92.29 | >98.0 |
| 4 | 2,4'-dichlorobenzophenone | 96.63 | 75.24 |
| 5 | 2-methoxycarbonylbenzophenone | 6.70 | 91.02 |
| 6 | 2-naphthylphenyl ketone | 98.80 | 64.60 |

COMPARATIVE EXAMPLE 7

Asymmetric hydrogenation of 2,4'-dichlorobenzophenone

Into a 100 ml stainless autoclave were fed a 0.2M solution of potassium hydroxide in 2-propanol (1.4 ml, containing 0.28 mmol of potassium hydroxide), (R,R)-diphenylethylenediamine (4.03 mg, 0.019 mmol), 2,4'-dichlorobenzophenone (1.26 g, 5.0 mmol), 2-propanol (3.31 ml), benzene (1.37 ml) and $Ru_2Cl_4[(R)\text{-BINAP}]_2NEt_3$ (8.45 mg, 0.005 mmol) under a nitrogen atmosphere. Then hydrogen gas was supplied thereinto so as to achieve a hydrogen pressure of 50 atm. After stirring at a reaction temperature of 50° C. for 20 hours, the reaction mixture was returned to ordinary temperatures and then concentrated under reduced pressure.

1.30 g of the residue thus obtained was purified by silica gel column chromatography (developer: hexane/ethyl acetate=4/1 to 2/1 by volume) to thereby give optically active 2,4'-dichlorobenzhydrol (1.183 g, yield: 93.4%). The optical purity of this 2,4'-dichlorobenzhydrol measured by high performance liquid chromatography was 60.62% e.e.

COMPARATIVE EXAMPLE 8

Asymmetric hydrogenation of 2,4'-dichlorobenzophenone

Into a 100 ml stainless autoclave were fed a 0.2M solution of potassium hydroxide in 2-propanol (1.4 ml, containing 0.28 mmol of potassium hydroxide), (R,R)-diphenylethylenediamine (4.03 mg, 0.019 mmol), 2,4'-dichlorobenzophenone (1.26 g, 5.0 mmol), 2-propanol (3.31 ml), benzene (1.37 ml) and $Ru_2Cl_4[(R)\text{-Tol-BINAP}]_2NEt_3$ (9.02 mg, 0.005 mmol) under a nitrogen atmosphere. Then hydrogen gas was supplied thereinto so as to achieve a hydrogen pressure of 50 atm. After stirring at a reaction temperature of 50° C. for 20 hours, the reaction mixture was returned to ordinary temperatures and then concentrated under reduced pressure.

1.41 g of the residue thus obtained was purified by silica gel column chromatography (developer: hexane/ethyl acetate=4/1 to 2/1 by volume) to thereby give optically active 2,4'-dichlorobenzhydrol (1.170 g, yield: 92.5%). The optical purity of this 2,4'-dichlorobenzhydrol measured by high performance liquid chromatography was 62.02% e.e.

The present invention provides an industrially advantageous process whereby optically active benzhydrol compounds, which have a high purity and are useful as, for example, intermediates in the synthesis of drugs, can be produced by simple procedures.

While the invention has been described in detail and with reference to specific embodiments thereof, it will be apparent to one skilled in the art that various changes and modifications can be made therein without departing from the spirit and scope thereof.

What is claimed is:

1. A process for producing an optically active benzhydrol compound represented by formula (II):

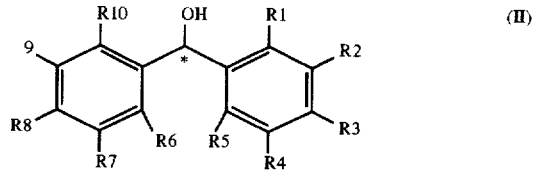

wherein $R^1$, $R^5$, $R^6$ and $R^{10}$ are the same or different and each represents a hydrogen atom, a halogen atom, a hydroxyl group, a lower alkyl group having 1 to 4 carbon atoms, a lower alkoxy group having 1 to 4 carbon atoms or a lower alkanoyl group having 1 to 5 carbon atoms; $R^2$, $R^3$, $R^4$, $R^7$, $R^8$ and $R^9$ are the same or different and each represents a hydrogen atom, a halogen atom, a hydroxyl group, a lower alkyl group having 1 to 4 carbon atoms, a lower alkoxy group having 1 to 4 carbon atoms, a lower alkanoyl group having 1 to 5 carbon atoms or an amino group optionally substituted by a lower alkyl group, a lower alkanoyl group or a lower alkoxycarbonyl group, $R^2$ and $R^3$, and $R^8$ and $R^9$ may be bonded to each other to thereby form —CH=CH—CH=CH—, and any two of $R^1$ to $R^9$ adjacent to each other may be bonded to thereby form —OCH$_2$O— or —(CH$_2$)$_3$—; and * shows the location of an asymmetric carbon atom;

which comprises hydrogenating a benzophenone compound represented by formula (I):

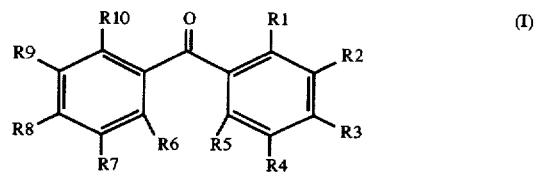

wherein $R^1$, $R^2$, $R^3$, $R^4$, $R^5$, $R^6$, $R^7$, $R^8$, $R^9$ and $R^{10}$ are each as defined above;

in the presence of a hydrogenation catalyst consisting of a transition metal complex represented by the following general formulae (III), (IV), (V) or (VI):

wherein X represents a halogen atom; L represents an optically active phosphine ligand; and A represents a tertiary amine;

wherein X and L are each as defined above; and E represents an optionally substituted benzene or p-cymene;

wherein L is as defined above; and G represents a halogen atom or an acetoxy group; or

wherein X and L are each as defined above; and J⁻ represents $BF_4^-$, $ClO_4^-$, $PF_6^-$ or $BPh_4^-$ wherein Ph represents a phenyl group, base and an optically active diamine compound, a said optically active phosphine ligand being represented by formula (VII):

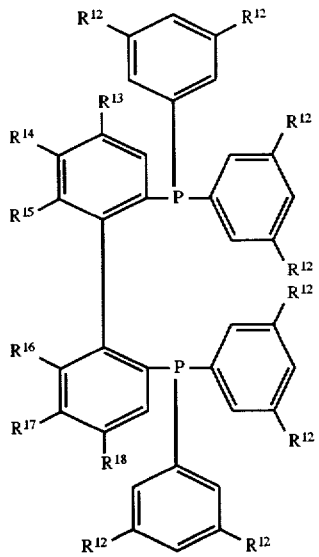
(VII)

wherein $R^{12}$ represents a lower alkyl group having 1 to 4 carbon atoms; $R^{13}$, $R^{14}$, $R^{15}$, $R^{16}$, $R^{17}$ and $R^{18}$ are the same or different and each represents a hydrogen atom, a lower alkyl group having 1 to 4 carbon atoms, a lower alkoxy group having 1 to 4 carbon atoms or a halogen atom, or $R^4$ and $R^{15}$ and $R^{16}$ and $R^{17}$ may be bonded to each other to thereby form a ring.

2. A process for producing an optically active benzhydrol compound as claimed in claim 1, wherein said optically active phosphine ligand is 2,2'-bis|di(3,5-di(lower alkyl) phenyl)phosphino|-1,1'-binaphthyl.

3. A process for producing an optically active benzhydrol compound as claimed in any one of claims 1 or 2, wherein said base is a compound represented by formula (XVIII):

MY$_n$ (XVIII)

wherein M represents an alkali metal atom or an alkaline earth metal atom; Y represents a hydroxyl group, an alkoxyl group or a mercapto group; and n is 1 or 2; or a quaternary ammonium salt.

4. A process for producing an optically active benzhydrol compound as claimed in any one of claims 1 or 2, wherein two carbon atoms having amino and/or substituted amino groups in the optically active diamine compound are adjacent to each other.

5. A process for producing an optically active benzhydrol compound represented by formula (II):

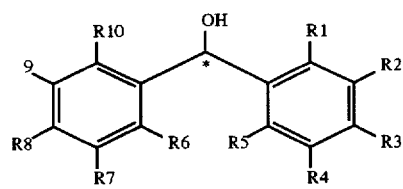
(II)

wherein $R^1$, $R^5$, $R^6$ and $R^{10}$ are the same or different and each represents a hydrogen atom, a halogen atom, a hydroxyl group, a lower alkyl group having 1 to 4 carbon atoms, a lower alkoxy group having 1 to 4 carbon atoms or a lower alkanoyl group having 1 to 5 carbon atoms; $R^2$, $R^3$, $R^4$, $R^7$, $R^8$ and $R^9$ are the same or different and each represents a hydrogen atom, a halogen atom, a hydroxyl group, a lower alkyl group having 1 to 4 carbon atoms, a lower alkoxy group having 1 to 5 carbon atoms, a lower alkanoyl group having 1 to 5 carbon atoms or an amino group optionally substituted by a lower alkyl group, a lower alkanoyl group or a lower alkoxycarbonyl group, $R^2$ and $R^3$, and $R^8$ and $R^9$ may be bonded to each other to thereby form —CH=CH—CH=CH—, and any two of $R^1$ to $R^9$ adjacent to each other may be bonded to thereby form —OCH$_2$O— or —(CH$_2$)$_3$—; and * shows the location of an asymmetric carbon atom;

which comprises hydrogenating a benzophenone compound represented by formula (I):

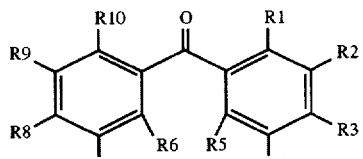
(I)

wherein $R^1$, $R^2$, $R^3$, $R^4$, $R^5$, $R^6$, $R^7$, $R^8$, $R^9$ and $R^{10}$ are each as defined above;

in the presence of a hydrogenation catalyst consisting of a transition metal complex represented by the following general formulae (III), (IV), (V) or (VI):

|Ru$_2$X$_4$(L)$_2$|(A) (III)

wherein X represents a halogen atom; L represents 2,2'-bis |di(3,5-di(lower alkyl)phenyl)phosphino|-5,5', 6,6', 7,7', 8,8'-octahydro-1,1'-binaphthyl; and A represents a tertiary amine;

|RuX(E)(L)|X (IV)

wherein X and L are each as defined above; and E represents an optionally substituted benzene or p-cymene;

[Ru(G)$_2$(L)] (V)

wherein L is as defined above; and G represents a halogen atom or an acetoxy group or

|RuX(L)|⁺J⁻ (VI)

wherein X and L are each as defined above; and J⁻ represents BF$_4$⁻, ClO$_4$⁻, PF$_6$⁻ or BPh$_4$⁻ wherein Ph represents a phenyl group, a base and an optically active diamine compound.

6. A process for producing an optically active benzhydrol compound represented by formula (II):

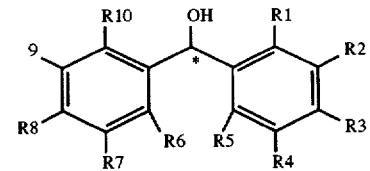
(II)

wherein $R^1$, $R^5$, $R^6$ and $R^{10}$ are the same or different and each represents a hydrogen atom, a halogen atom, a hydroxyl group, a lower alkyl group having 1 to 4 carbon atoms, a lower alkoxy group having 1 to 4 carbon atoms or a lower alkanoyl group having 1 to 5 carbon atoms; $R^2$, $R^3$, $R^4$, $R^7$, $R^8$ and $R^9$ are the same or different and each represents a hydrogen atom, a halogen atom, a hydroxyl group, a lower alkyl group having 1 to 4 carbon atoms, a lower alkoxy group having 1 to 4 carbon atoms, a lower alkanoyl group having 1 to 5 carbon atoms or an amino group optionally substituted by a lower alkyl group, a lower alkanoyl group or a lower alkoxycarbonyl group, $R^2$ and $R^3$ and $R^8$ and $R^9$ may be bonded to each other to thereby form —CH=CH—CH=CH—, and any two of $R^1$ to $R^9$ adjacent to each other may be bonded to thereby form —OCH$_2$O— or —(CH$_2$)$_3$—; and * shows the location of an asymmetric carbon atom;

which comprises hydrogenating a benzophenone compound represented by formula (I):

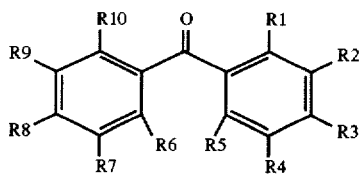

(I)

wherein $R^1$, $R^2$, $R^3$, $R^4$, $R^5$, $R^6$, $R^7$, $R^8$, $R^9$ and $R^{10}$ are each as defined above;

in the presence of a hydrogenation catalyst consisting of a transition metal complex represented by the following general formulae (III), (IV), (V) or (VI):

[Ru$_2$X$_4$(L)$_2$](A)  (III)

wherein X represents a halogen atom; L represents 2,2'-bis(diphenylphosphino)-5,5', 6,6', 7,7', 8,8'-octehydro-1,1'-binaphthyl; and A represents a tertiary amine;

[RuX(E)(L)]X  (IV)

wherein X and L are each as defined above; and E represents an optionally substituted benzene or p-cymene;

[Ru(G)$_2$(L)]  (V)

wherein L is as defined above; and G represents a halogen atom or an acetoxy group; or

[RuX(L)]$^+$J$^-$  (VI)

wherein X and L are each as defined above; and J$^-$ represents BF$_4^-$, ClO$_4^-$, PF$_6^-$ or BPh$_4^-$ wherein Ph represents a phenyl group, a base and an optically active diamine compound.

* * * * *

UNITED STATES PATENT AND TRADEMARK OFFICE
CERTIFICATE OF CORRECTION

PATENT NO. : 5,780,692
DATED : July 14, 1998
INVENTOR(S) : SAKAGUCHI, et al.

It is certified that error appears in the above-identified patent and that said Letters Patent is hereby corrected as shown below:

Column 16, line 10, delete formula (II) in its entirety, and insert the following formula:

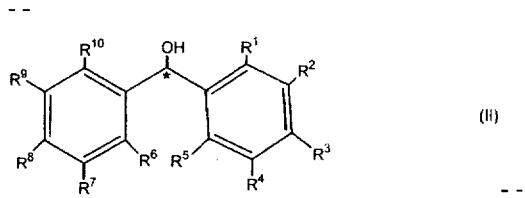

Column 17, lines 55-60, delete formula (II) in its entirety, and insert the following formula:

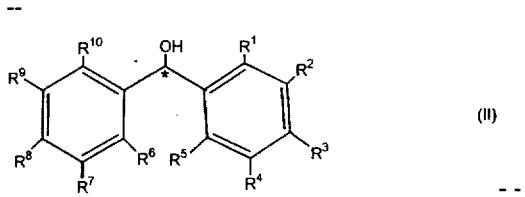

Column 18, lines 55-60, delete formula (II) in its entirety and insert the following formula:

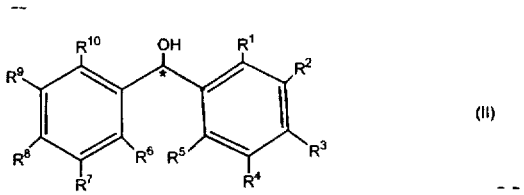

UNITED STATES PATENT AND TRADEMARK OFFICE
CERTIFICATE OF CORRECTION

PATENT NO. : 5,780,692
DATED : July 14, 1998
INVENTOR(S) : SAKAGUCHI, et al.

It is certified that error appears in the above-identified patent and that said Letters Patent is hereby corrected as shown below:

Column 16, lines 35-40, delete formula (I) in its entirety, and insert the following formula:

--

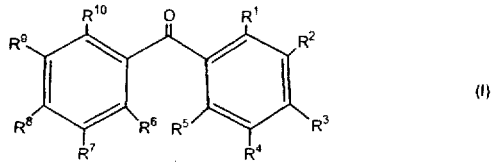

(I)

--

Column 18, lines 15-20, delete formula (I) in its entirety, and insert the following formula:

--

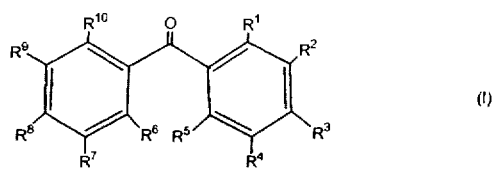

(I)

--

UNITED STATES PATENT AND TRADEMARK OFFICE
CERTIFICATE OF CORRECTION

PATENT NO. : 5,780,692
DATED : July 14, 1998
INVENTOR(S) : SAKAGUCHI, et al.

It is certified that error appears in the above-identified patent and that said Letters Patent is hereby corrected as shown below:

Column 19, lines 15-20, delete formula (I) in its entirety, and insert the following formula:

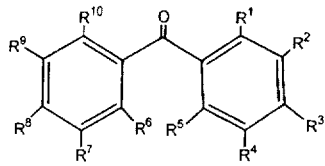

(I)

Signed and Sealed this

Twenty-first Day of March, 2000

Attest:

Q. TODD DICKINSON

Attesting Officer

Commissioner of Patents and Trademarks